United States Patent [19]

Auld

[11] 4,324,140

[45] Apr. 13, 1982

[54] ELECTRONICALLY SIMULATED ROTATING PRISM FOR ULTRASONIC BEAM SCANNING

[75] Inventor: Bertram A. Auld, Menlo Park, Calif.

[73] Assignee: The United States of America as represented by the Secretary of the Navy, Washington, D.C.

[21] Appl. No.: 174,292

[22] Filed: Jul. 31, 1980

[51] Int. Cl.³ .............................................. G01N 29/00
[52] U.S. Cl. ........................................ 73/602; 73/626; 73/642
[58] Field of Search .................. 73/602, 620, 625, 626, 73/642; 128/660; 367/103, 105, 122, 123, 125

[56] References Cited

U.S. PATENT DOCUMENTS

| | | | |
|---|---|---|---|
| 2,928,952 | 3/1960 | Bednarz | 250/216 |
| 3,656,828 | 4/1972 | Scholdstrom | 350/6.4 |
| 3,765,403 | 10/1973 | Brenden | 73/605 |
| 3,813,140 | 5/1974 | Knockeart | 350/6.8 |
| 3,835,448 | 9/1974 | Bertheas | 367/122 |
| 3,881,802 | 5/1975 | Helava | 350/6.8 |
| 4,016,750 | 4/1977 | Green | 73/629 |
| 4,030,344 | 6/1977 | Northeved et al. | 73/620 |
| 4,058,001 | 11/1977 | Waxman | 73/620 |
| 4,058,003 | 11/1977 | Macovski | 73/620 |
| 4,075,883 | 2/1978 | Glover | 73/620 |
| 4,084,582 | 4/1978 | Nigam | 73/620 |
| 4,233,678 | 11/1980 | Brady | 367/123 |
| 4,267,584 | 5/1981 | McKeighen et al. | 73/626 |

*Primary Examiner*—Stephen A. Kreitman
*Attorney, Agent, or Firm*—R. F. Beers; Charles D. B. Curry; George L. Craig

[57] ABSTRACT

A method and apparatus are described for electronically scanning a spherically focused beam in a c-scan mode using a spiral path rather than a traditional raster scan pattern. Essential to the technique is an electronically simulated rotating ultrasonic prism operating according to the general electrical input equation $V_{IN} = -V_o \exp(i\omega_o t + iA \cos \Omega t)$. The technique allows use of a single delay line with simple connections and no requirements of multiple mixing.

8 Claims, 5 Drawing Figures

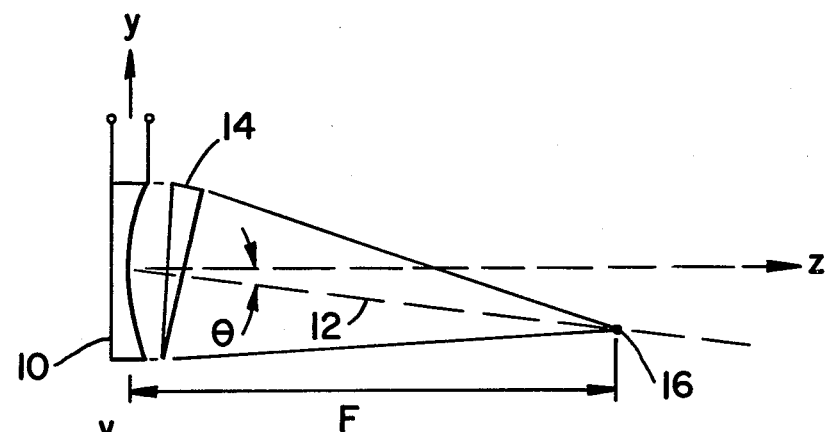
FIG_1
(PRIOR ART)
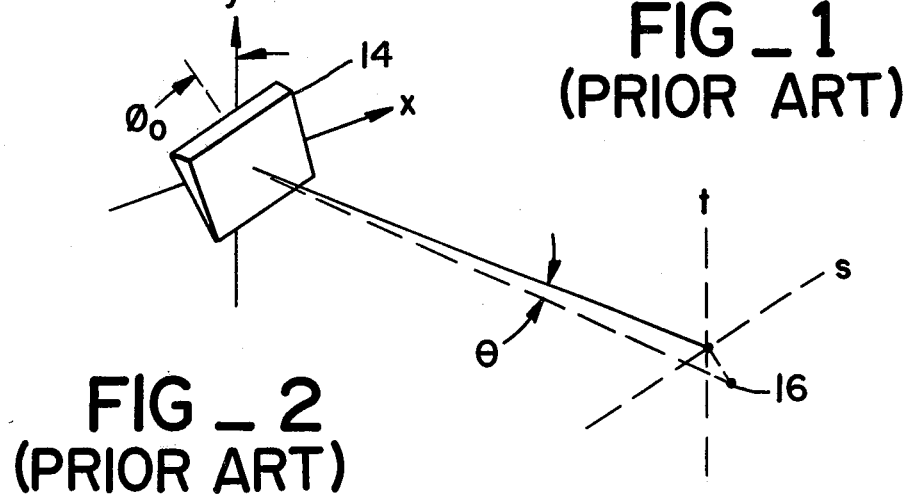
FIG_2
(PRIOR ART)
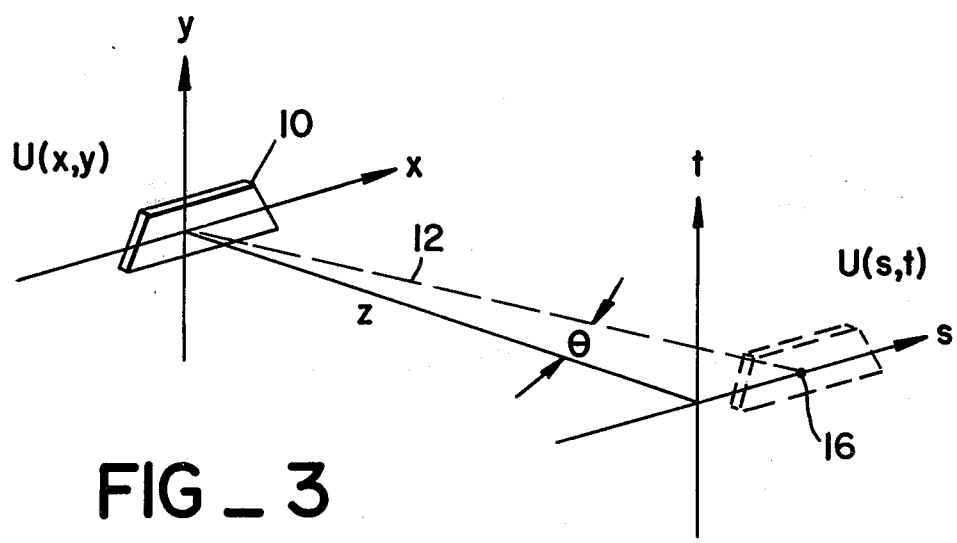
FIG_3

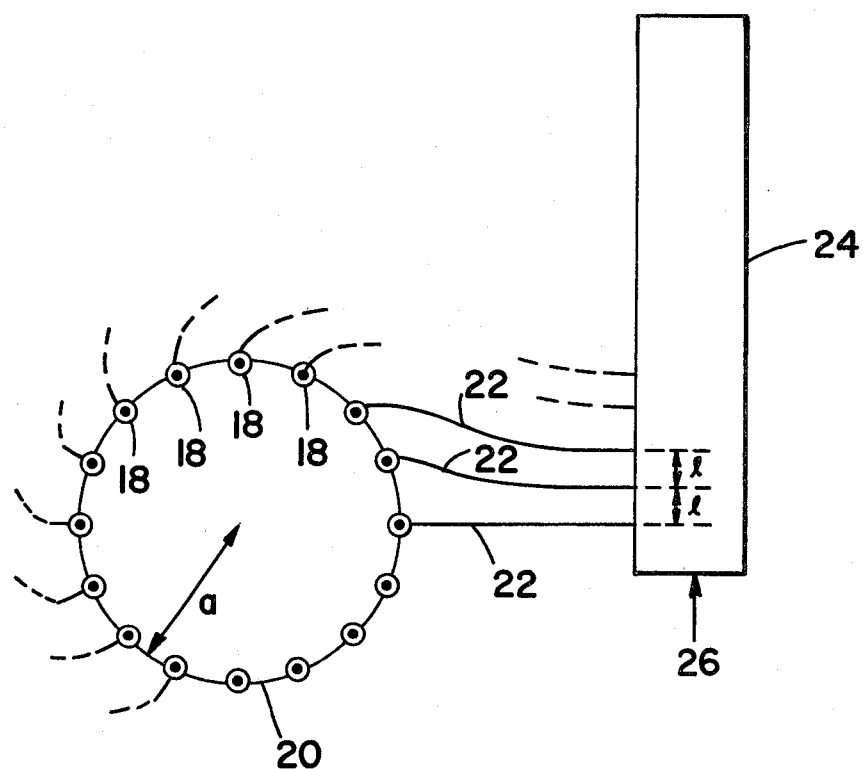
FIG_4
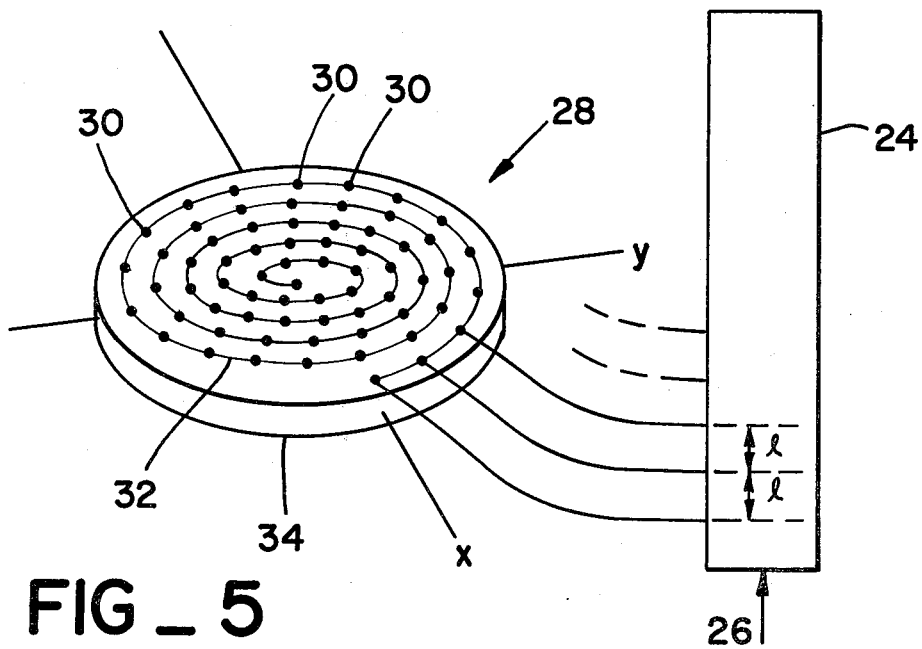
FIG_5

ELECTRONICALLY SIMULATED ROTATING PRISM FOR ULTRASONIC BEAM SCANNING

BACKGROUND OF THE INVENTION

1. Field of the Invention

The invention is related to an ultrasonic imaging device for clinical use in medicine. More specifically, the invention is related to a means for electronically simulating the rotating prism used in many conventional ultrasonic scanning devices.

2. Description of Prior Art

In recent years considerable activity has taken place to develop and produce rapidly-scanned ultrasonic imaging devices for clinical use in medicine. Such devices typically operate at megahertz frequencies and can be electronically focused and scanned. Generally, such devices use either ultrasonic or charge-coupled diode delay lines to provide the necessary phasing and time delay for focusing and scanning arrays of ultrasonic transducers. Conventional systems using such devices include B-type sectoral and raster scanners that are completely electronic in nature and a variety of C-type scanners. In the latter case the simplest system is a linear array that focuses and scans in one dimension and may be translated transversely by a mechanical motion in order to provide a two-dimensional image. More elaborate conventional systems consist of two orthogonally crossed linear arrays of the type described above, one array used as a transmitter and the other as a receiver in a transmission system scanned in two dimensions. This provides fully electronic two-dimensional scanning, with only 2 N transducer elements needed for $N^2$ resolvable spots. However, it is inefficient in that only the power at the intersection point of the two cylindrically focused beams is used for constructing the image. Even more elaborate conventional systems are possible consisting of two-dimensional arrays of transducers and capable of providing a spherically focused beam scanned in two dimensions over the C-plane. Such systems have the disadvantage of requiring complex mechanical arrays to provide a spinning prism, multiple delay lines, complex electromechanical interconnections and, generally, a double mixing process.

The instant invention avoids these disadvantages and limitations of the prior art by providing an electronically simulated rotating ultrasonic prism having an electronically variable focal length. This device provides a system capability for electronically scanning a spherically focused beam in a C-scan mode using a spiral path rather than a traditional raster pattern. The instant invention has no fragile rotating prism; requires only a single delay line; has very simple electromechanical interconnections; and does not require multiple mixing.

SUMMARY OF THE INVENTION

The instant invention is an apparatus and method for electronically simulating a rotating ultrasonic prism such that electronic scanning of a spherically focused beam in a C-scan mode is done in a spiral path rather than a traditional raster scan pattern. The invention has an electronically variable focal length and a single delay line.

A primary object of invention is to provide an ultrasonic scanning device for biomedical applications.

A further object of invention is to provide an ultrasonic scanning device having an electronically simulated rotating electronic prism.

Yet another object of invention is to provide an ultrasonic scanning device that scans in a C-scan mode using a spiral path rather than a typical raster scan pattern.

A yet further object of invention is to provide an ultrasonic scanning device having an electronically variable focal length.

Other objects, advantages and novel features will be apparent from the following detailed description when read in conjunction with the appended claims and attached drawings.

BRIEF DESCRIPTION OF THE DRAWINGS

FIG. 1 shows an ultrasonic beam deflected by a prism as practiced in prior art.

FIG. 2 shows a prism deflected and rotated ultrasonic beam as practiced by prior art.

FIG. 3 illustrates the deflection of an ultrasonic beam achieved by imposing an electronic linear phase variation.

FIG. 4 shows one embodiment of a transducer array permitting electronic simulation of a rotating ultrasonic prism.

FIG. 5 shows an alternate embodiment of a transducer array permitting electronic simulation of a rotating ultrasonic prism.

DESCRIPTION OF THE PREFERRED EMBODIMENT

Very many ultrasonic scanning devices use a prism placed in front of the ultrasonic beam to deflect it through some predetermined angle. A physical picture of the process as practiced in prior art is shown in FIG. 1 and FIG. 2. A geometrically focused ultrasonic transducer 10 acts as an aperture for the ultrasonic beam 12 and the prism 14 located in front of the transducer acts to deflect the ultrasonic beam through an angle $\theta$ to focal point 16. Since the transducer 10 is rotationally symmetric, rotation of the prism 14 through an angle $\Phi_o$ causes a rotation of the deflected beam 12 through the same angle and hence causes rotation of the focal point 16 in the focal plane. Mathmatically, this deflection and rotation process may be described by a phase modulation or "prism" function $$P(r,\phi) = \exp\left[ i \frac{\omega r \theta}{v_w} \cos(\phi - \phi_o) \right] \tag{1}$$

where $\Phi$ is measured from the positive y axis in FIG. 2 and the plus sign in the exponent comes from the fact that the ultrasonic velocity in the prism is greater than in water, the medium in which scanning occurs. If the prism 14 rotates at an angular velocity $$\Phi_o = \Omega t, \tag{2}$$

the focal point 16 scans a circular path at the same angular frequency. In the instant invention the effect of the rotating prism 14 can be simulated electronically by exciting the transducer 10 with a tapped delay line and by using a suitably shaped electrode pattern.

Referring to FIG. 3, the diffraction field 12 radiated by an ultrasonic transducer 10 of arbitrary shape has an aperture distribution function $U(x,y)e^{i\omega t}$. In the Fresnel region, the diffraction field at a distance z from the transducer 10 has an amplitude distribution function given by $$|U(s,t)| = \left| \iint_{\text{aperature}} \left\{ U(x,y)\exp\left[-i\frac{\omega}{2zv_w}(x^2+y^2)\right] \right\} \exp\left[i\frac{\omega}{zv_w}(sx+ty)\right] dxdy \right| \quad (3)$$

where $v_w$ is the velocity of ultrasound in a water medium. If the initial aperture distribution function is now modulated by the linear phase function $$P(x) = \exp\left[-i\frac{\omega x \sin\theta}{v_w}\right] \simeq \exp\left[-i\frac{\omega x \theta}{v_w}\right] \quad (4)$$

in the paraxial approximation, $\sin\theta \simeq \theta$, substitution of the equation $$U(x,y) \rightarrow P(x)U(x,y) \quad (5)$$

in the amplitude distribution function results in $$|U(s-z\theta,t)| = \left| \iint_{\text{aperature}} \left\{ U(x,y)\exp\left[-i\frac{\omega}{2zv_w}(x^2+y^2)\right] \right\} \exp\left[i\frac{\omega}{zv_w}((s-z\theta)x+ty)\right] dxdy \right| \quad (6)$$

That is, addition of the linear phase function deflects the diffraction pattern, and hence the focal point 16 of the radiated beam 12 through an angle $\theta$ in the st plane.

Referring to FIG. 4, a first embodiment of the instant invention is shown where the deflection and rotation of the ultrasonic beam may be achieved in electronic simulation of the rotating prism. Here, an array of small, circular transducers 18 is arranged uniformly around a ring 20 of radius a, large compared with the diameter of the individual transducers 18. There are N transducers 18 in the array spaced circumferentially at a distance small compared with the radius a, and each transducer 18 is connected to a set of taps 22 uniformly spaced at a distance 1 along a delay line 24. If a sinusoidal input signal 26 approximating $\sin\omega_o t$ is introduced into the delay line 24 and $$\frac{\omega_o l}{v} = 2\pi m \quad (7)$$

where v is the delay line velocity and m is some integer, the voltages at all taps 22 are in phase. This results in the Fresnel diffraction field being peaked on the array axis having a distribution given by $$U(s,t) = \sum_{n=0}^{\infty} a_n e^{in\phi} J_n\left(\frac{\omega_o a r}{zv_w}\right), \quad (8)$$

$$r^2 = s^2 + t^2 \quad \phi = \tan^{-1} - s/t$$

where n=0, N, 2N, etc. and the coordinates are as defined in FIG. 2. For a very closely spaced pattern of small transducers 18, the axial diffraction spot is closely described by the profile $$J_o\left(\frac{\omega_o a r}{zv_w}\right).$$

This peaked diffraction field distribution may be deflected and rotated according to the equation $$U(s,t) \longrightarrow U\left(s - \frac{\omega a \theta}{v_w}\sin\phi_o, t + \frac{\omega a \theta}{v_w}\cos\phi_o\right) \quad (9)$$

by imposing on the transducer array the spatial phase variation described by the prism function given previously. Generally, this would require that the phase be varied over each transducer 18 but in the instant invention where the diameter of the transducers 18 is small compared to the radius a of the ring 20 and there are many transducers 18 around the circumference, the phase of excitation at the $n^{th}$ transducer, located at angle $$\phi_n = \frac{2\pi n}{N} \quad (10)$$

is approximated by the discrete prism function given by $$P_n = \exp\left[i\frac{\omega_o a \theta}{v_w}\cos\left(\frac{2\pi n}{N} - \phi_o\right)\right] \quad (11)$$

To obtain the required array phasing for the instant invention, the input signal 26 is the phase modulated signal introduced into the delay line, $$V_{IN} = V_o \exp[i\omega_o t + iA \cos\Omega t] \quad (12)$$

where $A = (\omega_o a\theta/v_w)$, the multiplication factor for the circular geometry of the array $\omega_o$ = carrier frequency of the input signal $a$ = radius of the circle $\theta$ = angle through which the scanning beam is deflected $v_w$ = velocity of the scanning beam in water and $(\Omega l/v) = (2\pi/N)$.

The phase of the voltage at the $n^{th}$ electrode is then expressed by $$V_n = V_o \exp\left[i\omega_o\left(t - \frac{nl}{v}\right) + i\frac{\omega_o a \theta}{v_w}\cos\Omega\left(t - \frac{nl}{v}\right)\right] \quad (14)$$

Therefore the axial diffraction spot of the ultrasonic beam radiated by the array may be deflected through an angle $\theta$ and rotated at an angular frequency equal to the modulation frequency $\Omega$ in precise simulation of the rotating ultrasonic prism. To obtain a spiral scan, the amplitude of the input signal 26 is varied slowly as a linear function of time.

An alternate embodiment by which a rotating electronic prism may be simulated is by means of an unfocused disk transducer as shown in FIG. 5. The transducer 28 is in the shape of a plane disk having a full face electrode 34 on its bottom face. The top face of the transducer has an array of small electrodes 30 arrayed in a logarithmic spiral 32. These electrodes 30 are connected in succession to the taps of the delay line 24 similar to the first embodiment. However, because the radius r in the prism function previously described obviously varies appreciably over the transducer aperture, an input signal of different form than in the first embodiment must be used. If the angular spacing of the electrodes 30 is $2\pi/N$, the radial position of the $n^{th}$ tap in this embodiment is given by $$r_n = r_{max} \exp\left[-\alpha \frac{2\pi n}{N}\right] \text{ with } \alpha << 1 \tag{15}$$

and the input signal must be of the form $$V_{IN} = V_o \exp[i\omega_o t + iB \cos \Omega t] \tag{16}$$

where $$\text{where } B = \frac{\omega_o r_{max} \theta_{min} \exp[\alpha \Omega t]}{v_w},$$

the multiplication factor for the spiral geometry of the array
$r_{max}$ = maximum radial value of the outermost electrode of the spiral array
$\theta_{min}$ = minimum deflection angle of the scanning beam $\alpha < 0.015$
As in the first embodiment $$\frac{\omega_o l}{v} = 2\pi m \text{ and } \frac{\Omega l}{v} = \frac{2\pi}{N} \tag{17}$$

such that the voltage at the $n^{th}$ tap is given by $$V_n = \tag{18}$$

$$V_o \exp\left[i\omega_o t + i\frac{\omega_o r_n(\theta_{min} \exp[\alpha \Omega t])}{v_w} \cos\left(\frac{2\pi n}{N} - \Omega t\right)\right]$$

Comparing this with the prism function described previously shows that this voltage has the required phase variation. It also has a deflection angle that increases exponentially with time given by $$\theta(t) = \theta_{min} \exp[\alpha \Omega t] \tag{19}$$

and an angular velocity $\Omega$. The beam radiated by the transducer 28 therefore follows a spiral scan defined by the parameters above. When the required maximum deflection angle is reached at the end of the desired time frame, the exponential modulation is terminated and restarted for the succeeding frame.

If a focused disk transducer similar to the one shown in FIG. 2 is used rather than the unfocused disk transducer 28, the spiral electrode array may be used to provide a circular scan by simulating the rotating ultrasonic prism 14. As a circular scan attachment for this simulation, the full face electrode 34 is placed on the front face of the transducer 10 and the spiral array of electrodes 30 is placed on the back face. This circular scan simulated rotating prism has the added feature that the deflection angle $\theta$ is varied slowly with time providing a two-dimensional spiral coverage of the focal plane. The same scanning waveform of the input signal as just described is also used in this case.

What is claimed is:

1. Apparatus for electronically deflecting and rotating an ultrasonic scanning beam comprising:
  (a) means for generating ultrasonic energy;
  (b) means for transmitting electrical energy to said generating means;
  (c) means for delaying said electrical energy such that said transmitting means transmits electrical energy of predetermined phase to said generating means; and
  (d) an electrical input signal introduced as input to said delaying means, said electrical input signal having the form $V_{IN} = V_o \exp(i\omega_o t + iA \cos \Omega t)$, where A is a multiplication factor dependent on the geometry of said apparatus.

2. The apparatus of claim 1 wherein said generating means includes a plurality of transducers arrayed circumferentially equally spaced on a circle having radius much greater than the radius of each of said transducers, said transducers sequentially connected to said transmitting means.

3. The apparatus of claim 1 wherein said generating means includes:
  (a) an unfocused disk transducer having a top and a bottom side, said bottom side being a full face electrode; and
  (b) a plurality of electrodes arrayed in an equally spaced logarithmic spiral on said top side of said transducer, said electrodes being sequentially connected to said transmitting means.

4. The apparatus of claim 3 wherein said full face electrode is on said top face of said disk transducer and said electrodes arrayed in said logarithmic signal are on said bottom face of said disk transducer.

5. The apparatus of claim 1 wherein said transmitting means is a plural array of electrical taps.

6. The apparatus of claim 1 wherein said delaying means is a single delay line having said transmitting means connected to said delay line in a predetermined spaced array.

7. The apparatus of claim 2 wherein A of said electrical input signal has the form $(\omega_o a \theta / v_w)$ in which $\omega_o$ is the carrier frequency of said input signal, a is the radius of said circle, $\theta$ is the angle through which said scanning beam is deflected and $v_w$ is the velocity of said scanning beam in water.

8. The apparatus of claim 3 or 4 wherein A of said electrical input signal has the form $$\frac{\omega_o r_{max} \theta_{min} e^{\alpha \Omega t}}{v_w}$$

in which $r_{max}$ is the maximum radial value of the outermost of said electrodes in said spiral array, $\theta_{min}$ is the minimum deflection angle of said scanning beam and $\alpha$ is less than 0.015.

* * * * *